United States Patent [19]

Shenton

[11] 4,338,459
[45] Jul. 6, 1982

[54] USE OF ALKYLFORMAMIDE AND ACETAMIDE IN PREPARING α-ACETYL-α'-METHYLSUCCINATE ESTER

[75] Inventor: Francis L. Shenton, Portage, Mich.

[73] Assignee: The Upjohn Company, Kalamazoo, Mich.

[21] Appl. No.: 240,721

[22] Filed: Mar. 5, 1981

[51] Int. Cl.³ .................... C07C 67/00; C07C 69/716
[52] U.S. Cl. .................................... 560/176; 560/126
[58] Field of Search ........................................ 560/176

[56] References Cited

U.S. PATENT DOCUMENTS 3,213,155 10/1965 Schriesheim et al. ............. 562/496
4,194,053 3/1980 White .................................. 560/176

FOREIGN PATENT DOCUMENTS 2806424 9/1978 Fed. Rep. of Germany .

Primary Examiner—Vivian Garner
Attorney, Agent, or Firm—John T. Reynolds

[57] ABSTRACT

A diester of α-acetyl-α'-methylsuccinic acid is prepared in improved yield under substantially anhydrous process conditions which minimizes decomposition of that diester by reacting an acetoacetate ester with an α-halopropionate ester in a solvent mixture containing a nonpolar, aprotic liquid, e.g., toluene, and a dipolar aprotic liquid, e.g., DMF, at from about 50° C. to reflux temperature in the presence of a phase transfer agent, a catalytic amount of iodide ion and solid form, substantially anhydrous alkali metal base or basic salt. Further improvement is obtained when the completed reaction mixture is diluted with water and adjusted to pH 8 to 9, and when the DMF/acetoacetate ester ratios are between about 1.7 and 3. The resulting diesters can be used under the conditions of this invention as intermediates in processes for making ibuprofen by combining and reacting the α-acetyl-α'-methylsuccinate diester with vinyl isobutyl ketone (or the corresponding Mannich base plus an alkylating agent) and an alkali metal base, e.g., potassium tert-butoxide, for a time sufficient to form a reaction mixture containing the α-methyl-α'-acetyl-α'-(5-methyl-3-oxohexyl)succinate ester, which can then be converted to ibuprofen by procedures now known.

8 Claims, No Drawings

USE OF ALKYLFORMAMIDE AND ACETAMIDE IN PREPARING α-ACETYL-α'-METHYLSUCCINATE ESTER

DESCRIPTION

Introduction

This invention relates to processes for preparing derivatives of succinic acid esters, and to the use of those succinate ester derivatives in processes for making useful acid compounds. More particularly, this invention provides an improved process for preparing esters of α-acetyl-α'-methylsuccinic acid, which are useful as intermediates for preparing esters of α-methyl-α'-acetyl-α'-(5-methyl-3-oxohexyl)succinic acid and related compounds which are known to be useful in processes for preparing useful drug acids such as ibuprofen, and the like. This invention is most closely related to the invention described in U.S. application Ser. No. 938,972, filed Sept. 1, 1978, now U.S. Pat. No. 4,194,053, issued Mar. 18, 1980, as a continuation-in-part of U.S. application Ser. No. 778,571, filed Mar. 17, 1977, now abandoned.

BACKGROUND OF THE INVENTION

It is known that diethyl α-acetyl-α'-methylsuccinate can be prepared in about sixty-three percent yield by reacting ethyl acetoacetate with ethyl α-bromopropionate in the presence of sodium hydroxide, potassium iodide and water. Chem. Abs. 62, 13037c abstracting (Zh. Pukl. Khim, 38(2), pp. 436-7 (1965). Also, *J. Chem. Soc.* (London), 4633-40 (1970) reports that this same diester can be prepared in about forty-seven percent yield by reacting ethyl acetoacetate with ethyl α-bromopropionate in the presence of sodium in ethanol. Similar disclosures are found at Chem. Abs. 54, 10852h; Chem. Abs. 49, 1565c of *J. Chem. Soc.* (London) 3313 (1953); and Chem. Abs. 38, 2332 of *J. Ind. Chem. Soc.*, 20, 173-7 (1943).

David R. White, in the above-referenced application Ser. No. 938,972 and its predecessor application, described his findings that neither the aqueous basic system nor the ethanolic basic systems allowed the same alkylation to occur with the less expensive ethyl 2-chloropropionate in place of the ethyl 2-bromopropionate. He found that by using the 2-chloropropionate ester at moderate temperatures (40°-50° C.), no significant alkylation reaction was seen; under more vigorous (higher) temperature conditions, using these base systems, 2-chloropropionate and acetoacetate ester starting materials were consumed but little diethyl α-acetyl-α'-methylsuccinate ester accumulated in the product, evidencing that this valuable succinate ester intermediate is somewhat unstable and is further converted to undesired, useless by-products in those reaction mixtures.

The White application claims a process for preparing the diester of α-acetyl-α'-methylsuccinic acid comprising reacting an ester of acetoacetic acid with an ester of α-halopropionic acid wherein halo is chloro or bromo in a substantially anhydrous mixture of a nonpolar aprotic organic liquid having a dielectric constant below about 11 at 25° C., e.g., toluene, at a temperature of from about 50° C. to the reflux temperature of the mixture in the presence of a phase transfer agent, a catalytic amount of an iodide ion and a deprotonating base, e.g., potassium carbonate, having a surface area equivalent to a size below at least about 60 mesh, for a time sufficient to form the diester of the α-acetyl-α'-methylsuccinic acid. The above White applications are incorporated herein by reference for background and as an aid in describing elements used in this invention and distinctions therefrom.

Research on this and related chemical process steps to prepare ibuprofen from aliphatic starting materials continues. Somewhat surprisingly, it has been found according to this invention that the use of nonpolar, aprotic organic liquid of low dielectric constant, e.g., toluene, and the use of a deprotonating base of a particular particle size by Dr. White, is not necessarily the best way to obtain the highest practical yields of the necessary intermediate, the α-acetyl-α'-methylsuccinic acid ester. In my research I have raised the dielectric constant of the reaction mixture by adding a dipolar, aprotic liquid solvent and used larger particle size potassium carbonate than described by the White applications and come up with process improvements which not only raise the yields of the above succinate ester intermediate but have defined a process improvement which is more compatible with the chemical steps which follow toward the synthesis of the end product, ibuprofen.

For additional background to the use of α-acetyl-α-methylsuccinate esters in processes for preparing useful drug acid compounds, see British Pat. No. 1,265,800 and Belgian Pat. No. 820,267.

OBJECTS OF THE INVENTION

It is an object of this invention to provide an improved and more economical process for preparing esters of α-acetyl-α'-methylsuccinic acid.

It is a more specific object of this invention to provide an improvement on the above-described White process for preparing α-acetyl-α-methylsuccinate diesters which improves the yields of such diesters.

It is a further object of this invention to provide an improvement in the process for preparing α-acetyl-α'-methylsuccinate diesters from acetoacetic acid esters and 2-halopropionate esters, which is more compatible with subsequent steps in the overall process of preparing ibuprofen as an end product.

Other objects, aspects and advantages of this invention will become apparent from the description and claims which follow.

SUMMARY OF THE INVENTION

Briefly, by this invention I have discovered that by adding a specific type of a dipolar, aprotic solvent, e.g., DMF, to the toluene mixture of the acetoacetate and 2-halopropionate esters that the yields of the α-acetyl-α'-acetyl-methylsuccinate ester intermediate product can be increased and that this dipolar, aprotic solvent addition obviates the need to mill and pre-dry the potassium carbonate or other deprotonating base to smaller particle size than is readily available from suppliers before being added to this reaction mixture. Moreover, I have also discovered that specific ratios of the dipolar, aprotic solvent in the reaction mixture and the use of an aqueous acid dilution of the reaction mixture after completion of the reaction to bring the pH of the mixture to about pH 8 to 9, to separate base and the dipolar, aprotic solvent prior to work-up of the mixture to recover the α-acetyl-α-methylsuccinate ester in usable form, also enhance the yields of the α-acetyl-α'-methylsuccinate ester. Optionally, and perhaps preferably for larger scale operations of the process, the succinate ester product reaction mixture can be filtered, and the resulting liquid phase treated with an aqueous medium to extract the dipolar, aprotic solvent from the organic liquid phase containing the succinate ester, for reuse in the process. This use of DMF as the added dipolar, aprotic solvent in the reaction mixture also makes preparation of the crude succinate ester product more compatible with process steps which follow.

DETAILED DESCRIPTION OF THE INVENTION

More specifically, this invention provides a process for preparing an α-acetyl-α'-methylsuccinate diester which comprises reacting an ester of acetoacetic acid with an ester of 2-halopropionic acid wherein halo is chlorine or bromine in a substantially anhydrous liquid solvent mixture of (a) a nonpolar, aprotic organic liquid having a dielectric constant below about 11 at 25° C., and (b) a dipolar, aprotic organic liquid solvent having a dielectric constant over 25 at 25° C., e.g., a di-$C_1$ to $C_4$-alkylformamide or di-$C_1$ to $C_4$-alkylacetamide at a temperature of from about 50° C. to the reflux temperature of the mixture in the presence of a phase transfer agent, a catalytic amount of an iodide ion and a deprotonating base for a time sufficient to form the diester.

Examples of nonpolar, aprotic organic liquids having a dielectric constant below about 11 at 25° C. are benzene, chlorinated benzenes, toluene, xylene, ethyl benzene, and the like, with toluene being preferred over benzene for employee safety purposes and because it has an optimum boiling point range for azeotroping out water which might enter the reaction mixture with reactants, catalysts, base, etc.

Examples of the di-$C_1$ to $C_4$-alkylformamide and di-$C_1$ to $C_4$-alkylacetamides which can be used to dilute the toluene or other nonpolar, aprotic solvents are dimethylformamide (DMF), diethylformamide, dipropylformamide, dibutylformamide, and the corresponding di-$C_1$ to $C_4$-alkylacetamides, e.g., dimethylacetamide (DMAC), etc., with the DMF being preferred for reasons of economy, ready availability, and its efficiency.

I have found that the better yields of the α-acetyl-α'-methylsuccinate esters are obtained when the mole ratios of DMF, or other dipolar, aprotic organic solvent in the reaction mixture (at the start of the reaction) is between about 1.7 to about 3.0, relative to the mole content of the acetoacetate ester in the mixture. Preferably, the molar content of the DMF is started at about 2.6 to 2.8, relative to the acetoacetate ester content, to obtain the best yields. An added benefit is that with DMF, or other equivalent dipolar, aprotic solvent in the reaction mixture, the optimum reaction time is shortened to about 1.5 hours at 100° to 105° C. With the same DMF ratios, the maximum yields of the succinate we have obtained have been about 73 percent at 90° C., 74 percent at 109° C. and 62 percent at 114° C. The amount of deprotonating base, e.g., potassium carbonate, in the mixture can vary in the molar ratio range of from about 1 to about 1.5 molar equivalent of the deprotonating base per molar equivalent of the acetoacetate ester in the mixture. I have found that a molar ratio of about 1.3 molar equivalent of base, preferably potassium carbonate, per molar equivalent of acetoacetate ester gives the best results. With 1.3 molar equivalents of potassium carbonate as deprotonating base, relative to acetoacetate ester, the yield of α-acetyl-α-methylsuccinate ester is about 77 percent.

With the aid of this invention either "milled" or "granular" potassium carbonate can be used. Granular potassium carbonate is the form normally obtained from suppliers thereof. Milled (ground to smaller particle size) potassium carbonate still gives better yields than the use of the granular form, but the granular form can now be used with the new added DMF, or other dipolar, aprotic solvent addition process. Attempts to conduct the process using granular potassium carbonate in 100 percent toluene as the only solvent for the reactants (no DMF or other dipolar, aprotic solvent present) gave yields of 25–40 percent. The more important feature or advantage of this invention with respect to the potassium carbonate is that the potassium carbonate, whether milled or not, can now be used successfully, without predrying. That is, the potassium carbonate can be dried in situ in the solvent mixture before the reactants are added to the reaction vessel.

Our best laboratory yields to date have been in the 82 to 85 percent yield range, using milled potassium carbonate and a ratio of about 2.6 molar equivalent of the DMF per mole of acetoacetate ester reactant, with a work-up of the reaction mixture including an aqueous extraction of the reaction mixture to remove the salts and DMF from the succinate ester/toluene phase at a pH of about 8.5. Without the use of DMF, or equivalent dipolar, aprotic solvent, the yield of succinate ester varies in the range of 50 to 74 percent and the potassium carbonate must be carefully predried.

Our current best pilot plant scale manufacturing procedure for this new improved process gives about 70 percent yield of succinate ester when granular potassium carbonate is used and workup of the reaction mixture involves only filtration of the mixture to remove solid salts from the liquid reaction mixture, then aqueous extraction of the toluene liquid phase to remove DMF therefrom. The aqueous wash here need not be controlled to pH 8 to 9, if the salts have been removed from the reaction mixture, but such pH 8 to 9 wash procedure can be used. In the manufacturing procedure, this filtration/aqueous procedure has a significant economic and engineering advantage of separating DMF from the salts, thus allowing recovery and recycle of the DMF. More recently, we have obtained higher yields in the pilot plant manufacturing process approaching 85 percent yield of succinate ester by using milled potassium carbonate instead of granular potassium carbonate.

Thus, even though better yields of succinate ester product might be obtained using the laboratory procedure (pH 8–9 wash), other economic and engineering factors dictate the use of the filtration/aqueous wash manufacturing procedure for best production yields of this α-acetyl-α-methylsuccinate diester product of this process.

We consider this discovery to be somewhat surprising and unique because other dipolar, aprotic solvents having similar high dielectric constants such as N-methyl-2-pyrrolidone (dielectric constant 32.2) were tried since DMF (dielectric constant 36) was more effective than dimethylsulfoxide (DMSO; dielectric constant 45), but the yield of succinate ester with N-methyl-2-pyrrolidone was seven percent lower than with DMF under the same conditions. Formamide was tried and it gave poor results.

Without intending to be bound to particular theory of how or why the invention works to improve the yields of the succinate ester intermediate product, we offer the following as a possible explanation of what might happen in the reaction mixtures according to this invention.

Yields of the succinate ester in this process step probably depend upon my discovery of how to maximize the rate of succinate ester formation in the reaction mixture while minimizing the rates of undesired by-product formation. DMF was the most effective of the dipolar, aprotic solvents tried, particularly at about 100° C., but the other named dipolar, aprotic solvents can be used. At lower than the desired reaction temperature range, succinate ester is not formed rapidly enough to keep up with by-product formation, while at higher temperatures than about 105° C., the succinate ester cyclizes to lactones nearly as fast as it forms, thus lowering the yields of the usable succinate ester. DMF, and equivalent dipolar, aprotic solvents, seem to selectively accelerate succinate ester formation, probably by selective complexation with the anion of ethylacetoacetate, as opposed to the anion of succinate. Another factor possibly contributing to the higher yields of succinate ester according to the process of the invention, is the enhanced dissolution/dispersion of the potassium carbonate or other deprotonating base in the mixture, which dissolution/dispersion could increase the rate of anion formation in the reaction mixture. The amount of DMF or other dipolar, aprotic solvent in the mixture apparently needs to be adjusted to account for both of these anion formation and dissolution/dispersion factors. Since the rate of reaction seems to depend upon the available surface area of deprotonating base in the mixture, lower amounts of DMF or other dipolar, aprotic solvent may complex with and perhaps agglomerate some of the solid base, e.g., potassium carbonate particles. If the low amount of DMF or other dipolar, aprotic solvent causes agglomeration of solid base particles, and thus perhaps reduces the amount of base available for reaction, the yield of succinate ester would be lowered, as observed when only 1.0 molar equivalent of deprotonating base, e.g., potassium carbonate, is used. With DMF molar ratios, relative to the acetoacetate ester reactant, much higher than the 3.0 ratio, the complexation of anions in the reaction mixture probably is no longer selective, so that there may be an acceleration of the cyclization of succinate ester product to by-product lactone, thus lowering the yield of the desired succinate ester product. It is interesting to note that the optimum amount of DMF, or other dipolar, aprotic solvent in the mixture, usually corresponds roughly to the sum of the molar equivalents of the potassium carbonate (or other deprotonating base) and the acetoacetate reactant in the mixture. Overall, in laboratory scale operation of the process, the yields of succinate ester according to the improved process of this invention are increased by using both DMF in the reaction mixture and a pH 8.5 work-up, the description of which follows:

When the reaction between the α-acetyl-α-methylsuccinate and 2-halopropionate ester is complete, the reaction mixture is diluted with water to extract from the organic reaction mixture the base, water soluble materials including the DMF or other dipolar, aprotic solvent and to separate the dipolar, aprotic solvent from further contact with the succinate ester intermediate product. Addition of an acid, preferably any economical, readily available mineral acid, such as 2 to 10 percent sulfuric acid, to adjust the pH of the aqueous phase to between 8 and 9, preferably to about 8.5, has been found to enhance the separation of the succinate ester organic solution from unwanted materials and DMF. The water added to the succinate ester containing reaction mixture can be the acid solution itself or the acid can be added later. One or more washes of the toluene or other organic liquid phase with water may be done to ensure cleaner succinate ester product. The organic phase containing the succinate ester can then be treated to purify and isolate the succinate ester by known procedures, or prepare it in usable form, particularly for use in the next step of the process. For this latter purpose, we obtain the succinate ester in usable, but crude form by evaporating off most of the organic solvent to leave as residue the crude succinate ester. We have found it sufficient to evaporate the organic solvent under a vacuum pressure of 40 mm. Hg. to 65°–70° C. Then this residue succinate ester can be used as a reactant in the next step of the overall process for preparing ibuprofen.

As indicated above, when this invention is applied to use in pilot plant or manufacturing scale operation of the process, economic and engineering factors may dictate that the pH 8–9 aqueous wash of the reaction mixture step be avoided, in favor of a simple filtration or centrifuging of the reaction mixture to separate solids (salts, such as potassium carbonate, potassium iodide, etc.) from the organic liquid mixture, followed by extraction (washing) of the organic liquid reaction mixture with water (pH control optional) to extract the DMF, or other dipolar, aprotic liquid from the non-aqueous miscible phase (e.g., toluene phase) containing the succinate ester product, and then to separate the liquid phases, and evaporate the succinate ester liquid phase, preferably under vacuum pressure, to remove most if not all of the nonpolar organic liquid from the succinate ester product.

The next step in such process is a Michael condensation reaction between this α-acetyl-α'-methylsuccinate ester and isobutyl vinyl ketone to form a mixture of products having the following general formulae:

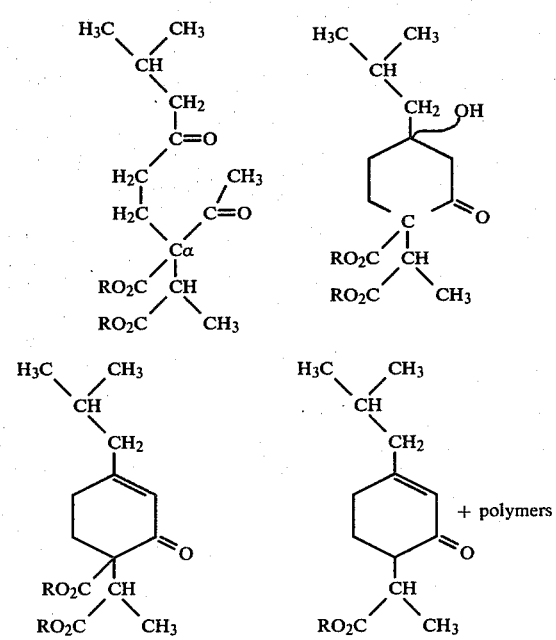

where each R is a $C_1$ to $C_4$-alkyl.

The process improvement of this invention fits nicely with the process improvements described in U.S. application Ser. No. 047,391, filed June 11, 1979. With DMF being the preferred dipolar, aprotic solvent to use in each of these two process steps, the burden of solvent recovery for reuse in the overall process becomes easier, thus requiring the recovery of only toluene, or other nonpolar, aprotic organic solvent and DMF, or other dipolar, aprotic organic solvent, instead of toluene and DMF (for my improvement) and DMSO, as originally contemplated in the Michael addition reaction step.

The invention is described and exemplified further by the detailed examples which follow:

EXAMPLE 1

First Use of DMF in Reaction Mixture

A mixture of 20.7 g. of milled, calcined potassium carbonate, 1.5 g. each of 60 mesh potassium iodide and Aliquat 336 (believed to be tricaprylmethylammonium chloride), 15.0 ml. each of ethyl 2-chloropropionate and ethyl acetoacetate and 1.0 ml. of docosane and 50 ml. of toluene is stirred under nitrogen at about 100° C. with 5.0 ml. of DMF added. The reaction is monitored over 6.5 hours, during which the temperature ranged from 61° to 102° C. and is maintained mostly at 102° C. The reaction mixture turns from white to light yellow to yellow. Samples are taken periodically to analyze and monitor the amount of succinate product in the reaction mixture. After 6.5 hours the oil bath heat is lowered and the reaction mixture is cooled to 45° C. in thirty minutes. Then 100 ml. of water is added. The reaction mixture is then analyzed by gas liquid chromatographic (glc) methods and found to contain 143.3 mg./ml. of diethyl α-acetyl-α'-methylsuccinate for a 55.7% chemical yield.

EXAMPLE 2

Use of DMF Together With pH 8.5 Work-up Procedure

The procedure of Example 1 is followed, except that 25 ml. toluene and 25 ml. DMF are used, and the heating of the reaction mixture is done for a shorter period of time (one hour, fifty minutes), during which the temperature is raised from 51° C. to 104° C. The reaction mixture is cooled to 35° C. over thirty-five minutes and then 110 ml. of water is added with stirring. Then 10 percent sulfuric acid in water solution is added until the pH of the aqueous phase is about 8.5, and then the reaction mixture is worked up to recover the diethyl α-acetyl-α'-methylsuccinate product. Analysis of the reaction mixture by glc procedures shows it to contain 262.6 mg. of the acetyl succinate product per ml. A yield of 82.8 percent chemical is obtained.

This example illustrates that a shorter reaction time and a less basic work-up of the reaction mixture (pH about 8.5) seems to be effective to obtain higher yields.

EXAMPLE 3

Process Run Without Milling The Potassium Carbonate

A mixture of 22.1 g. of regular, granular, non-milled or dried, technical potassium carbonate, 23.0 ml. of technical DMF, 1.5 g. of Aliquat 336 and 27 ml. of toluene are stirred at reflux until no more water azeotropes out of the mixture to dry the potassium carbonate and the reaction mixture. A total of 0.6 ml. of water is collected. Then 14.5 ml. each of ethyl acetoacetate (114.3 mmoles) and 14.5 ml. of ethyl 2-chloropropionate and 1.5 g. of potassium iodide and 1.0 g. of n-docosane are added at room temperature and the resulting mixture is stirred and heated for three hours and five minutes over which time the temperature rises from 60° C. to 104° C. and then back down to 100.5°–101.5° C. The mixture is treated with water and aqueous ten percent sulfuric acid solution to raise the pH to 8.5 and analyzed to determine the content of the diethyl α-acetyl-α'-methylsuccinate ester product. Glc analysis shows the mixture to contain 168.2 mg./ml. of product, so that 113 ml. of reaction mixture contains 19.01 g. for a 72.4 percent chemical yield.

This experiment is believed to evidence a real breakthrough in this process research. Even without milled or dried potassium carbonate, and using a high dielectric constant solvent (DMF) the reaction went reasonably well, comparable to the previous standard, operating procedure using milled, dried potassium carbonate with no DMF.

EXAMPLE 4

Succinate Preparation—Larger Scale Optional Procedure

A slurry of 267 kg. calcined, granular potassium carbonate, 19.3 kg. each of potassium iodide, and Aliquat 336, 311 kg. of DMF, and 276 l. of toluene was stirred at reflux (118°–120°) for two hours while water was azeotroped off and collected in a trap. The resulting dried slurry was cooled to below 80° C. Then 189 kg. of ethyl acetoacetate and 198 kg. of ethyl 2-chloropropionate were added and the reaction mixture was stirred at 103°±3° C. for ninety minutes.

120 kg. toluene was added and the reaction mixture was cooled to 20° C. The salts were filtered off using a centrifuge and the filtrate (toluene plus product) was washed with water (once with 280 l. water, then twice with 140 l. water each wash). The combined aqueous washes were backwashed with 85 kg. toluene. The combined toluene phases were concentrated under vacuum at 65° C. to leave 348 kg. (350 l.) of crude α-acetyl-α'-methylsuccinate diester, assay 663 mg./ml. for a yield of 69 percent chemical.

The procedure as described above was repeated, except that the $K_2CO_3$ was milled to <200 mesh before use. The yield with this modification was 85 percent chemical.

I claim:

1. A process for preparing an α-acetyl-α'-methylsuccinate diester which comprises reacting an ester of acetoacetic acid with an ester of α-halopropionic acid wherein halo is chloro or bromo in a substantially anhydrous liquid solvent mixture of (a) a nonpolar, aprotic organic liquid having a dielectric constant below about 11 at 25° C. and (b) between about 1.7 to about 3.0 moles of a dipolar, aprotic organic liquid solvent selected from the group consisting of a di-$C_1$ to $C_4$-alkylformamide and a di-$C_1$ to $C_4$-alkylacetamide relative to the mole content of the acetoacetate ester in the mixture at a temperature of from about 50° C. to the reflux temperature of the mixture in the presence of a phase transfer agent, a catalytic amount of an iodide ion and a solid form deprotonating base for a time sufficient to form the diester.

2. Process according to claim 1 wherein the ester radicals of the acetoacetate and the α-halopropionate esters are $C_1$ to $C_6$-alkyl radicals.

3. A process according to claim 1 wherein (a) the nonpolar, aprotic organic liquid has a dielectric constant below about 5 at 25° C., and (b) the dipolar, aprotic organic liquid is a di-$C_1$ to $C_4$-alkylformamide.

4. Process according to claim 3 wherein (a) the nonpolar, aprotic organic liquid is benzene, toluene, or xylene, and (b) the dipolar, aprotic organic liquid is dimethylformamide.

5. Process according to claim 4 wherein ethyl acetoacetate and ethyl α-halopropionate are heated together in a liquid mixture containing (a) benzene, toluene, or xylene and (b) dimethylformamide, in the presence of potassium carbonate, potassium iodide, and Aliquat 336 at 90° to 110° C. for a time sufficient to form diethyl α-acetyl-α'-methylsuccinate.

6. Process according to claim 1 wherein the molar equivalent ratio of dimethylformamide to acetoacetate ester in the reaction mixture is stirred in the range of from about 2.6 to about 2.8, relative to the molar content of the acetoacetate in the mixture.

7. Process of claim 1 which further includes the step of treating the reaction mixture from claim 1 with water and an acid to adjust the pH of the aqueous portion of the mixture to from about 8 to 9, prior to work-up of the mixture to recover the α-acetyl-α'-methylsuccinate ester from the nonpolar organic liquid phase.

8. Process of claim 7 wherein the reaction mixture is treated with water and aqueous mineral acid in an amount sufficient to adjust the pH of the mixture to about 8.4 to about 8.6, prior to work-up of the mixture to recover the α-acetyl-α'-methylsuccinate in usable form.

* * * * *

UNITED STATES PATENT AND TRADEMARK OFFICE
CERTIFICATE OF CORRECTION

PATENT NO. : 4,338,459
DATED : July 6, 1982
INVENTOR(S) : Francis Lee Shenton

It is certified that error appears in the above—identified patent and that said Letters Patent is hereby corrected as shown below:

On the title page

[73] Delete "The Upjohn Company" and replace with --The Upjohn Manufacturing Company M--

Column 9, line 16, Claim 6: Delete "stirred" and replace with --started--.

Signed and Sealed this

Second Day of November 1982

[SEAL]

Attest:

Attesting Officer

GERALD J. MOSSINGHOFF

Commissioner of Patents and Trademarks